United States Patent [19]

Narang et al.

[11] Patent Number: 4,617,384

[45] Date of Patent: Oct. 14, 1986

[54] ADAPTOR MOLECULES FOR DNA AND THEIR APPLICATION TO SYNTHESIS OF GENE-DERIVED PRODUCTS

[75] Inventors: Saran A. Narang, Ottawa, Canada; Ray J. Wu, Ithaca, N.Y.

[73] Assignee: Cornell Research Foundation, Inc., Ithaca, N.Y.

[21] Appl. No.: 426,457

[22] Filed: Sep. 29, 1982

Related U.S. Application Data

[63] Continuation of Ser. No. 129,880, Mar. 27, 1980, abandoned.

[51] Int. Cl.[4] .................. C07H 21/04; C12N 15/00
[52] U.S. Cl. .................. 536/27; 435/172.3
[58] Field of Search .................. 536/27-29; 435/172, 172.3

[56] References Cited

U.S. PATENT DOCUMENTS 4,237,224 12/1980 Cohen et al. .................. 435/172
4,293,652 10/1981 Cohen .................. 536/27
4,321,365 3/1982 Wu et al. .................. 536/27
4,371,625 2/1983 Trollars .................. 435/317

FOREIGN PATENT DOCUMENTS 7900399 1/1980 PCT Int'l Appl. .

OTHER PUBLICATIONS

Villa 14 Konaroff, et al., Proc. Natl. Acad., Sci., vol. 75, 3727 (1978).
Heyneker, H., et al., Nature, vol. 263, p. 748-752, 1976.
Method in Enzymology, vol. 68, Wu, ed., pp. 98-109, 1979.
Pribnow, Proc. Nat. Acad. Sci., vol. 72, pp. 784-788, 1975.
Marians, K., et al., Nature, vol. 263, pp. 744-748, 1976.
Ullrich, A., et al., Proceeding of the Symposium on Proinsulin, Insulin and C-Peptide, Tokushima, Jul. 12-14, 1978, pp. 20-26.
Itakura, K., et al., Science, vol. 198, pp. 1056-1066, 1977.
Crea, R., et al., Proc. Natl. Acad. Sci., vol. 75, pp. 5763-5769, 1978.
Bahl, P. et al., Gene 1, pp. 81-92, 1976.
Scheller, R., et al., Science, vol. 196, pp. 177-180, 1977.
Goeddel, D. et al., Proc. Natl. Acad. Sci, vol. 76, pp. 106-110, 1979.
Goeddel, D. et al., Nature, vol. 281, pp. 544-548, 1979.
Polisky et al., Proc. Nat. Acad. Sci., vol. 73, pp. 3900-3905, 1976.
Roberts, Directory of Restriction Endonucleses, *Methods in Enzymology*, 68: 24-41 (1979).
Brevet et al, *DNA Insertion Elements, Plasmids and Episomes*, 1977, Cold Spring Harbor Labs.
Lehninger, *Biochemistry*, 1970, Worth Publishers p. 718.

Primary Examiner—Blondel Hazel
Attorney, Agent, or Firm—Jones, Tullar & Cooper

[57] ABSTRACT

Adaptor molecules have been prepared to comprise either start or stop signals for protein synthesis, in addition to recognition sites for restriction endonucleases. Separate adaptors may be used in a symmetrical duplex form. The start adaptor may include nucleotide base inserts to provide the correct reading frame of the triplet code in a DNA sequence with inappropriate reading frame. Insulin A-chain and B-chain genes of the human type, have been synthesized with the appropriate adaptor molecules provided on each end. The adapted DNA genes have been joined to replicable cloning vehicles and the hybrid DNA transferred to a host cell. The transformed host cell has been shown to contain the desired insulin gene.

16 Claims, No Drawings

ADAPTOR MOLECULES FOR DNA AND THEIR APPLICATION TO SYNTHESIS OF GENE-DERIVED PRODUCTS

This is a continuation of application Ser. No. 129,880 filed Mar. 27, 1980 now abandoned.

FIELD OF THE INVENTION

This invention is concerned with DNA information sequences, novel adaptor molecules for these sequences and the joining of the resulting adapted sequences into replicable cloning vehicles. Of particular concern are genes and adapted genes coding for the A and B chains of insulin, the insertion of these adapted genes into cloning vehicles, and the transferring of the hybrid DNA molecules into host cells, the transformed cells thus having the ability to produce the specified insulin chains.

BACKGROUND AND PRIOR ART

In very recent years, methods have been developed (see "Molecular Cloning of Recombinant DNA", eds., W. A. Scott and R. Werner, Academic Press Inc., 1977)

(1) for the in vitro joining by DNA ligase of a DNA segment to be cloned (scheme 1, structure I) to a cloning vehicle (DNA capable of independent replication, structure II), (2) for introducing the hybrid DNA molecule (recombinant DNA, structure III) into a suitable cell, (3) for selecting and identifying the transformed cells carrying the desired hybrid DNA (cloned DNA as a hybrid DNA, structure IV), (4) for amplifying the desired cloned DNA in the transformed cells, and (5) for expressing the cloned DNA as a protein product.

In most reported cases, DNA molecules isolated from cells or viruses have been fragmented by restriction enzyme digestion or by physical shearing before cloning.

Scheme 1
The cloning of a DNA fragment in a bacterium.
The dots at the ends of DNA molecules represent the proper sequence that allows matching and ligation of the ends with other DNA molecules

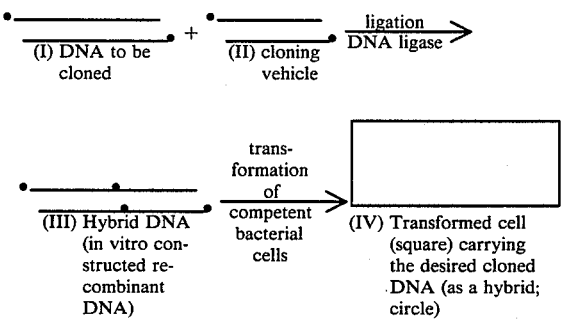

Protein synthesis in bacteria at a site located within a transferred DNA segment derived from mouse was shown by Chang et al. (Cell 6, 231–244, 1975). Still other examples of the cloning of natural foreign DNA have been described recently.

Methods for the total chemical synthesis of oligodeoxynucleotides of up to 20 nucleotides long, have been well established by using either the phosphodiester method (Khorana, H. G., J. Mol. Biol. 72, 209, 1972) or the improved phosphotriester method (Hsiung, H. M., and Narang, S. A., Nucleic Acids Res. 6, 1371, 1979; Narang, S. A. et al., Methods in Enzymology, Vol. 65, 610, 1979, and Vol. 68, 90, 1979). The latter method is now the preferred method because of its higher speed, better yield and purity of products, and has been used to prepare defined DNA sequences of longer length.

A few chemically-synthesized DNA sequences, such as the lactose operator (Marians, Wu et al., Nature 263, 744, 1976) and the tyrosine tRNA gene (Khorana, Science 203, 614, 1979), have been successfully cloned in E. coli and the expression of the cloned DNA detected in subsequent cultures. Recent reports have indicated that human brain hormone somatostatin (14 amino acids) has been produced in a transformed bacterial host which had the transferred synthesized gene (Itakura et al., Science 198, 1056, 1977). More recently, reports have appeared that human growth hormone has been produced in bacteria transformed with transferred genetic material comprising the appropriate gene. This latter gene was prepared by copying to DNA part from isolated mRNA (from human pituitary) and synthesizing the remaining part, then joining the two (Goedell et al., Nature 281, 544, 1979).

In the pancreas of animals, preproinsulin (Chan, S. J. and Steiner, D. F., Proc. Nat. Acad. Sci. 73, 1964, 1976) is synthesized as the precursor of insulin. The general structure of proinsulin (Formula 1) is $NH_2$-B chain-(C peptide)-A chain-COOH; it is converted to insulin by the action of peptidases in the pancreatic islet tissue which removed the C peptide by cleavage at the positions of the two arrows shown in Formula 1. The B-chain and A-chain of insulin are held together by two disulfide cross-linkages.

Using a biological method, Ullrich et al., (Science 196, 1313, 1977) and Villa-Komoroff, et al., (Proc. Nat. Acad. Sci. 75, 3727, 1978) succeeded in cloning the coding region of rat proinsulin I. However, the cloned gene included extraneous sequences and production of biologically active insulin was not achieved. Using a chemical method, Crea et al. (Proc. Nat. Acad. Sci. 75, 5765, 1978) synthesized, and Goeddel et al. (Proc. Nat. Acad. Sci. 76, 106, 1979) cloned, an insulin A-chain gene and a B-chain gene. The codons selected for these synthetic genes were arbitrary and quite different from the natural human DNA sequence. The construction of these genes was tedious. On culturing, the bacteria produced an insulin A-chain protein and B-chain protein which were separately treated to remove the extraneous β-galactosidase and methionine. The production of A-chain and B-chain proteins was rather poor.

In U.S. patent application Ser. No. 843,422, filed Oct. 19, 1977, by R. Wu, C. P. Bahl and S. A. Narang, adaptor molecules were described for attachment to the ends of DNA sequences for joining to cloning vehicles or other DNA. These adaptors comprise DNA (oligonucleotide) sequences having particular nucleotide segments which are recognition sites for restriction endonucleases. These adaptors can be used to provide an enzyme recognition site on a duplex DNA sequence or to change from one type of site to another.

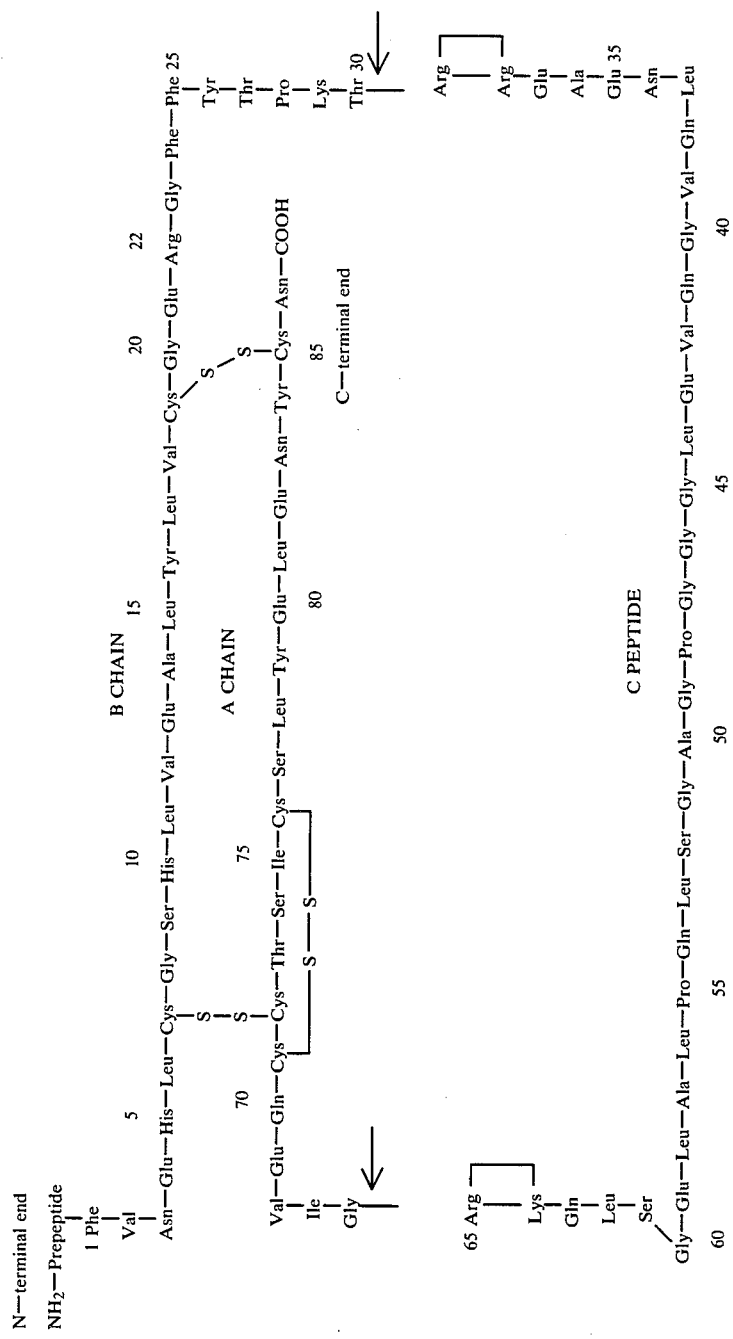
Formula 1.
The structure of human proinsulin. B chain, amino acids 1–30; C peptide, amino acids 31–65; A chain, amino acids 66–86.

SUMMARY OF THE INVENTION

Adaptor oligodeoxynucleotide molecules are provided for facilitating insertion of DNA information sequences into a cloning vehicle and transcription and translation of said sequences in a host cell; each adaptor comprising: (a) a recognition site for a restriction endonuclease, and (b) a signal for protein synthesis, selected from a start signal and a stop signal, said start signal being downstream of said recognition site and said stop signal being upstream of said recognition site.

In each "start" adaptor, the start signal(s) will always be located downstream of the restriction endonuclease recognition site; in each "stop" adaptor, the stop signal(s) will always be located upstream of the recognition site. Each "start" or "stop" signal is one codon (base triplet) long, but more than one codon may be used together to reinforce the signal. The "start" or "stop" codons are selected and positioned to cause the desired DNA information sequence to be read or translated correctly and exclusively in every case thus to assure a high yield of mRNA and ultimate protein in the host cell. In many cases, start signal adaptor molecules will need to include at least one additional base between each start signal and the recognition site to correct the frame shift of a DNA information sequence with inappropriate reading frame. The ATG codon is the basic "start" signal, although the GTG codon may be used instead.

The "stop" signal is one (or more) codon(s) selected to ensure that the translation in the host cell ceases at precisely the right location to give the correct protein (without subsequent modifications being required). Codons found to be particularly suitable are at least one from the group TGA, TAA and TAG.

The adaptors are preferably formed and used as separate molecules (Bahl et al., Gene 1, 81, 1976), but in some cases, may be built up on the end of a DNA information sequence (Marians, Wu et al., Nature 263, 744, 1976).

Many of these separate adaptor molecules which are to be attached to a DNA information sequence, preferably will be prepared as short duplex DNA sequences including the recognition site and signal, the signal being at both ends of the duplex so that the complete adaptor molecules have rotational symmetry along a two-fold axis (X and Y). In other words, these symmetrical adaptors are DNA duplexes having duplicate signals at each end, each complementary nucleotide strand having complete palindromic symmetry to its opposite strand, with both halves of the duplex being identical on 180° rotation of one half. Either end of the adaptor can attach to the DNA with increased efficiency (see example with insulin A-chain below). Such start signal adaptors can include additional nucleotide bases between each start signal and the central recognition site, to correct the frame shift of a DNA information sequence with inappropriate reading frame.

Synthetic genes coding for the A-chain and B-chain of human-type insulin have been prepared, provided with selected "start" and "stop" adaptors as described above, and inserted into a replicable cloning vehicle. This vehicle or vector is extrachromosomal DNA which can enter a cell and replicate itself, such as a plasmid. The synthetic gene + cloning vehicle hybrid has been inserted into a host cell, and the transformed host cell progeny was shown to contain the exact input insulin A-chain or B-chain gene by DNA sequence analysis.

DETAILED DESCRIPTION AND PREFERRED EMBODIMENTS

Typical adaptors having start or stop signals can be depicted respectively as follows (in duplex form):

Formula 2a

```
                                    start
5'  CAT  | recognition |  ATG
3'  GTA  |    site     |  TAC
```

Formula 2b

```
    stop
5'  TGA  | recognition |  TCA
3'  ACT  |    site     |  AGT
```

Formula 2c

```
    stop
5'  TAA  | recognition |  TTA
3'  ATT  |    site     |  AAT
```

Formula 2d

```
    stop
5'  TAG  | recognition |  CTA
3'  ATC  |    site     |  GAT
```

These duplexes are seen to have rotational symmetry so that either end can attach to the genetic information sequence without side product formation. The recognition sites themselves have this rotational symmetry. A typical symmetrical duplex adaptor having a double stop signal and a Bam HI site is shown in Formula 2e:

Formula 2e

```
5'  TGA TAG GGATCC  CTA TCA
3'  ACT ATC CCTAGG  GAT AGT
            Bam HI
             site
```

The adaptors can have from about 8 to about 20 or more nucleotide base pairs (or incomplete pairs) in their structure. The symmetrical adaptors will require an even number.

The enzyme recognition sites can be selected from those known for suitable restriction endonucleases (over 100 are now known). In the examples below, we have used as the recognition site (the boxed-in region) the Bam HI site GGATCC and the Eco RI site GAATTC.

```
CCTAGG            CTTAG
```

The part of this sequence which serves as the protruding cohesive end after cleavage, is 5' GATC for Bam HI, and 5' AATT for Eco RI (the complete recognition sequence less the two end bases). The cohesive end portions of the recognition sequences of other restriction endonucleases are derived similarly depending on the digestion cleavage location. For example, for Hind III the protruding cohesive sequence would be AGCT;

for Xba I, CTAG; and for Ava II, GAC or GTC. Other restriction endonucleases and their recognition sequences are described in, for example, the article by H. O. Smith in Science, Vol. 205, p. 455, Aug. 3, 1979 (see Table 1, p. 458), and by R. J. Roberts, in Gene, Vol. 4, p. 183, 1978. Preferably the enzyme recognition sequence duplex has a cleavage pattern that, on digestion, leaves a protruding part of at least 3 bases, and more preferably 4. When used herein, "recognition site" is meant to include the partial site which is recognized and adhered to by the complementary portion.

The DNA information sequence may be a duplex DNA which can be isolated from a natural source (such as from microorgansims, plant cells or animal cells) or it may be synthesized chemically or enzymatically. It will code for some desired gene-derived product.

In some cases, the genetic information sequence to be transferred may have a faulty frame shift. By attaching one or more base pairs between the "start" signal and the enzyme recognition sequence on the adaptor molecules, the reading frame of the triplet code can be corrected by means of the adaptors. For example, the reading frame of the non-overlapping triplet genetic code as it follows through the cloning vehicle and adaptor sequence may end up at the start signal, e.g. as in Formula 3a.

Formula 3a

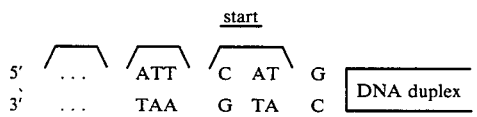

This will cause the DNA information duplex to be read incorrectly. By inserting one or two nucleotide pairs X in the adaptor (between the start signal and the Y recognition site) the reading frame can be shifted as shown in Formula 3b:

Formula 3b

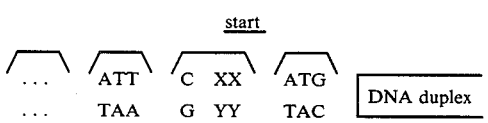

In some cases it may be desirable to insert one complete codon plus one, or -plus two nucleotide pairs (i.e. 4 or 5 nucleotide pairs). The X and Y can be any nucleotides: with bacterial host cells T and A usually are preferred. These inserts will enable the DNA to be read correctly. In the case where the rotationally symmetrical adaptor is used, corresponding base pairs should be inserted on both sides of the enzyme recognition site to maintain the two-fold rotational symmetry of the adaptor molecule. The advantage of such symmetrical adaptors is to assure the correct joining to DNA in every case and thus give good yields of the desired adapted DNA sequence (where full duplex is attached to DNA duplex). An example of such a symmetrical start signal adaptor is given in the following formula 3c:

Formula 3c

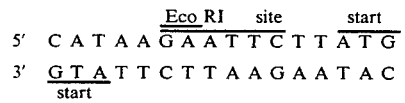

These adaptor sequences have been prepared by an improved phosphotriester method as described in U.S. patent application Ser. No. 843,422, referred to above, and including techniques as described in Nucleic Acid Res. 7, 2199, 1979, and in the Hsiung et al. and Narang et al. references mentioned above. An outline of the synthesis of a 12-nucleotide-long start signal adaptor is given below for formula 5a and for its digested form (left side of formula 3d). The duplex adaptors can be prepared, then joined to each end of the gene (or DNA duplex to be cloned) and digested to give the protruding cohesive ends. In some cases (particularly where the gene is being synthesized), steps can be designed to yield the protruding 5' recognition site and signal without digesting the full adaptor duplex, as illustrated below for the insulin B-chain.

When attaching the first adaptor duplex to the gene duplex (as by DNA ligase), it has been found desirable, in order to minimize side products, to make the 5'-terminus at the opposite end of the gene 5'-OH. After joining this first adaptor, the 5'-OH end is made 5'-OP by using ATP and polynucleotide kinase, and the second adaptor joined. When the two adaptor duplexes are joined, the product is digested with the appropriate restriction enzyme(s) to produce the cohesive ends. The resulting digested adapted DNA sequence or gene will have the structure 3d (for example, where the Eco RI and Bam HI enzyme sites were used with the start and stop adaptors respectively). X and Y are the optional nucleotide inserts to correct the reading frame and Z is 0, 1 or 2 (or 4 or 5).

Formula 3d

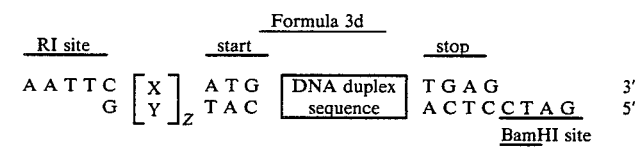

The adapted genetic information sequence having protruding cohesive ends which are part of the recognition site (and are recognized by the complementary part of the site), is now ready for insertion into a replicable cloning vehicle having complementary sites for cohesion. Suitable cloning vehicles may be plasmids, plasmid fragments, viruses, viral DNA fragments, and other cellular DNA pieces (usually at least about 3000 nucleotides long). The adapted DNA molecule (gene) and the cloning vehicle which has been treated with appropriate endonuclease, can be joined by use of a polynucleotide ligase such as $T_4$ ligase. Preferably the cloning vehicle DNA will include a transcription promoter sequence such as the lac promoter or tryptophan promoter placed upstream of the inserted gene.

A-CHAIN INSULIN GENE

Of particular concern are genes coding for human insulin A- and B-chains and these will be described in detail as preferred embodiments of the invention. The amino acid sequence of human insulin A-chain is shown in formula 4a upper line, from amino acid number 66 to 86. This sequence is identical to that of rat insulin A-chain except that amino acid no. 69 is aspartic acid in rat insulin. Ullrich et al. (cited above) described the codon sequence of mRNA (and DNA) for rat insulin A-chain. Drawing in part from this sequence and from other knowledge, and using instead the codon GAG for glutamic acid, a mRNA and partial duplex DNA sequence was put together as shown in formula 4a and 4b. This sequence we selected is much closer to the natural human DNA sequence than that selected by Crea et al., mentioned above. We synthesized the DNA H strand of 43 nucleotides and separately the DNA L strand of 36 nucleotides (as in formula 4a) using the phosphotriester method as described previously. The two strands were partially complementary and formed the partial duplex as shown. To complete the synthesis of the 63-nucleotide-long duplex DNA, we made use of primer-extension repair-synthesis techniques to complete the full duplex DNA gene. These repair-synthesis techniques are described by R. Wu et al., in Methods in Cancer Research 12, 87, 1976. The overlapping of 16 nucleotides between the H- and L-strands was sufficient to allow efficient repair-synthesis by AMV reverse transcriptase at 37° C., or by E. coli DNA polymerase at 5°–15° C. In this way, we reduced the rather time-consuming effort required for the chemical synthesis of the entire two strands. The sequence of the resulting DNA was analyzed in part and confirmed by the chemical method of Maxam and Gilbert (Proc. Nat. Acad. Sci. 74, 560, 1977). This human A-chain gene differs from that described by Crea et al. (cited above) by having some different codons which are closer to the natural codons used for human insulin gene and having no extragenous DNA sequences so that this "as synthesized" gene can be joined directly to insulin chain B-C gene to construct a proinsulin gene (chain B-C-A) with no improper codons intervening.

---

Formula 4a
Amino acid sequence of human insulin A chain and the corresponding mRNA and DNA sequence. The designation of the H- and L-strands of DNA are arbitrary.

Amino acids (A-chain) human insulin
66       70              76            80              86
Gly.Ile.Val.Glu.Gln.Cys.Cys.Thr.Ser.Ile.Cys.Ser.Leu.Tyr.Gln.Leu.Glu.Asn.Tyr.Cys.Asn mRNA
5' GGC.AUU.GUG.GAG.CAG.UGC.UGC.ACC.AGC.AUC.UGC.UCC.CUC.UAC.CAA.CUG.GAG.AAC.UAC.UGC.AAC. 3'

DNA (H)
5' GGC.ATT.GTG.GAG.CAG.TGC.TGC.ACC.AGC.ATC.TGC.TCC.CTC.TAC.C           3'
    5      10     15     20     25     30     35    40

DNA (L)
3'                                       TAG.ACG.AGG.GAG.ATG.GTT.GAC.CTC.TTG.ATG.ACG.TTG. 5'
                                         36                                                           1

---

Formula 4b
Construction of human insulin A-chain gene. The roman numerals indicate the specific oligodeoxynucleotide fragments synthesized chemically.

DNA (H)
         I                       II                III             VIII
*pGGC.ATT.GTG.GAG.CAG.TGC.TGC.ACC.AGC.ATC.  TGC.TCC.CTC.TAC.C  G.GAG.AAC.TAC
5'     5      10     15 20      25     30      35    43

DNA (L)
                                                                                                                1
TC.GTC.ACG.ACG.T  TAG.ACG.AGG.GAG.ATG.GTT.GAC.CTC.TTG.ATG.ACG.TTG-OH
3'                                                                                                    5'
      VII            IV             V            VI

---

In constructing the synthetic human insulin A-chain gene, each of the chemically synthesized oligodeoxynucleotides (fragment I through VIII, formula 4b) was phosphorylated at its 5'-ends with $^{32}P$. The phosphorylation reaction for each oligodeoxynucleotide (2 nmoles) includes 50 mM glycine-NaOH (pH 9.5), 10 mM $MgCl_2$, 10 mM dithiothreitol, 5 nmoles of $[\epsilon-^{32}P]ATP$ of specific activity of around 20 mCi/$\mu$-mole, and 3 units of $T_4$ polynucleotide kinase in a final volume of 50 $\mu$l. The reaction was carried out at 37° C. for 2 hours; during this time from 50 to 70 percent of the oligodeoxynucleotide was phosphorylated. The desired product was purified by polyacrylamide gel electrophoresis (15% gel, under denaturing conditions).

The 43-nucleotide-long upper strand (see formula 4a, H strand) was assembled by annealing 500 pmoles each of 5'-phosphorylated oligonucleotide fragments I, II, III, IV and VII in 15 $\mu$l at 65° and slowly cooled to 0° C. Concentrated ligase buffer was added to give the following final concentrations: 50 mM Tris-HCl (pH 7.6), 10 mM $MgCl_2$, 10 mM dithiothreitol, 100 $\mu$M ATP. $T_4$ polynucleotide ligase (0.4 unit) was added and the mixture incubated at 12° C. for 24 hours. The ligation product was purified on a 15% polyacrylamide gel (denaturing condition). The desired 43-long oligodeoxynucleotide migrated to about 46% that of the bromophenol blue dye marker. The yield of purified 43-long product after elution from the gel was around 50 pmoles. The 36-nucleotide-long lower strand (formula 4a, L strand) was assembled in a similar manner using phosphorylated oligonucleotide fragments III, IV, V, VIII and non-phosphorylated fragment VI.

The 63-nucleotide-long duplex (63-mer) A-chain insulin gene was constructed by annealing about 40 pmoles each of the 5'-$^{32}$P 43-long and the 5'-OH 36-long oligodeoxynucleotides. Repair synthesis was carried out, to fill in the single-stranded regions, in 50 mM Tris-HCl (pH 8.3), 50 mM KCl, 10 mM MgCl$_2$, 10 mM dithiothreitol, 100 μg/ml bovine serum albumin, 100 μM each of dGTP, dATP, dTTP and [α—$^{32}$P]dCTP (specific activity around 4 mCi/μmole), and 9 units of avian myeloblastosis virus reverse transcriptase in a final volume of 20 μl. Incubation was at 37° C. for 3 hours. The desired products were purified by polyacrylamide gel electrophoresis and two strands of the 63-mer were separated (migrated to about 72% that of the xylene cyanol dye marker). DNA sequence analysis of the eluted 63-long products (pilot scale with high specific activity $^{32}$P-dCTP) showed the correct sequence for the A-chain insulin gene.

The cloning of this insulin A-chain gene was controlled by adding both a start signal and a stop signal for protein synthesis (in the adaptors described above) to the two ends of the synthetic gene. Not only can this adapted DNA be joined to the cloning vehicle but after cloning and transcription, the initiation and termination of insulin protein (A-chain) synthesis can be achieved.

The dodecadeoxynucleotide adaptor duplex containing a start signal downstream of the restriction endonuclease recognition site was synthesized using the phosphotriester methods to have the structure:

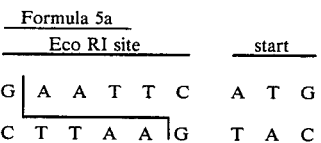

Similarly, a stop signal adaptor was synthesized to have the structure:

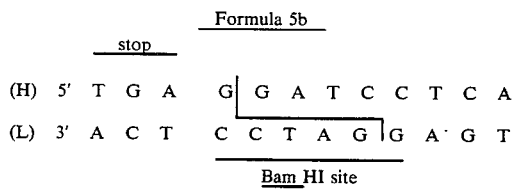

The 5' terminus at the tail end of the A-chain gene was kept in its 5'-OH form and the start signal adaptor 5a joined to the head end using T$_4$ polynucleotide ligase by blunt-end ligation as follows. The reaction mixture contained 50 mM Tris-HCl (pH 7.6), 10 mM MgCl$_2$, 10 mM dithiothreitol, 100 μM ATP, 200 pmoles of the self-complementary 12-mer start-signal adaptor (5a), 25 pmoles of 63-mer duplex A-chain gene, and 0.25 units of T$_4$ polynucleotide kinase in a final volume of 15 μl. Incubation was at 12° C. for 40 hours. Small scale gel electrophoresis of an aliquot of the reaction mixture with and without Eco RI enzyme digestion showed that about 50% of the 63-mer duplex was ligated to a start-signal adaptor. The DNA in the main portion of the reaction mixture was extracted with chloroform:isoamyl alcohol (24:1 v/v) and precipitated with 2 volumes of ethanol. The tail end 5'-OH was then converted to 5'-OP using ATP$^{32}$ and polynucleotide kinase (as before). Next the stop signal adaptor 5b was ligated to the tail end of the A-chain gene to give the adapted gene. The adapted gene was digested successively with Eco RI and Bam HI restriction enzymes to produce the respective cohesive ends (and to remove any additional start or stop signals ligated to the gene).

A cloning vehicle was prepared, by cutting out and purifying on an agarose gel, a 4000-nucleotide-long fragment from pBR 322 plasmid with both Eco RI and Bam HI enzymes. This fragment (0.5 μg) had cohesive ends which were then ligated by DNA ligase (as before) to the complementary part of the enzyme recognition sites on the adapted insulin A-chain gene (about 1 pmole).

This gene-cloning vehicle hybrid (one-half of the sample) was used to transform cells of *E. coli* (strain 5436). This strain and the containment facilities used conformed to current recombinant DNA regulations. One-hundred and ten ampicillin (trademark)-resistant and tetracycline-sensitive transformants were isolated. On being hybridized with $^{32}$P-labelled short synthetic insulin A-chain DNA fragments (30–35 bases long) by colony hybridization (Grunstein & Hogness, Proc. Nat. Acad. Sci. 72, 3961, 1975) 22 positive clones were obtained. Direct DNA sequence analysis (Maxam and Gilbert method) was carried out on several of the positive clones to confirm the presence of the insulin A-chain gene in the hybrid plasmid DNA. The DNA fragment excised, by digestion with both Eco RI and Bam HI enzymes, from three clones showed by direct DNA sequence analysis the exact nucleotide sequence as synthesized.

The cloned insulin A-chain gene on pBR 322 plasmid was prepared in increased quantities by growing *E. coli* cells carrying this hybrid plasmid in M9 medium until the optical density of the cell culture equalled about 1 at 600 nm. Chloramphenicol was added to give a final concentration of 150 mg/L. The cells were shaken at 37° C. for another 12 to 16 hours. The hybrid plasmid DNA in the cells was isolated according to standard procedure (such as that of Marians et al., Nature 263, 744, 1976).

The cloned insulin A-chain gene was next excised by digestion of the cloned hybrid plasmid DNA with Eco RI and Bam HI endonucleases. The Bam HI end was converted to an Eco RI and by using an Eco RI-Bam HI conversion adaptor of the type reported by Bahl et al. (Biochem. Biophys. Res. Commun. 81, 695, 1978) except that the double-stranded portion of the adaptor was increased from 6-long to 8- or 10-long to increase the efficiency of ligation. The conversion adaptor has the structure:

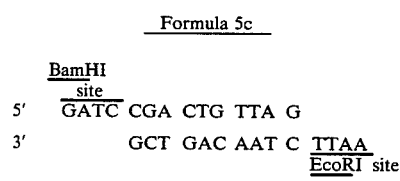

The resulting adapted insulin A-chain gene carrying an Eco RI site at each end, with the following type of structure:

Formula 5d

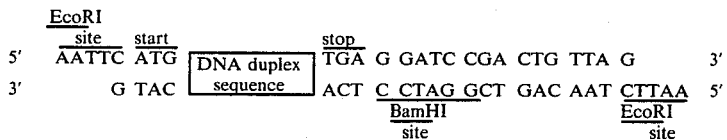

can be ligated to a plasmid such as pBGP120 (Polisky et al., Proc. Nat. Acad. Sci. 73, 3900, 1976), or a high copy number plasmid (such as pKN402 of Uhlin et al., Gene 6, 91, 1979) carrying a strong promoter (such as the lactose promoter, the strain being constructed in our laboratory) for expression. This reconstructed hybrid plasmid DNA can be ligated at the Eco RI sites and used to transform $E.$ $coli$ cells to direct the synthesis of large amounts of the human insulin A-chain protein. The flow of information from DNA to protein is by transcribing the DNA sequence into a complementary messenger RNA (mRNA sequence) and then translating the mRNA sequence (using the 3 letter genetic code) in the synthesis of a protein.

Still other plasmids or replicable DNA sequences would be operative as cloning vehicles.

For good yields of such transferred-gene-derived products, the culture medium for the host cells should be one that favors the reproduction of the inserted DNA hybrid, as well as transcription, translation and expression of desired product. Such culture media can be of the type designated M9 as described in J. Bacteriol. 119, 450, 1973, L. Katz and D. R. Helinski. These media contain nutrients that favor the replication of plasmids and other replicable cloning vehicles (as well as protein synthesis). Further such media are described in "Experiments in Molecular Genetics" by J. M. Miller, page 431, 1972, Cold Spring Harbour Lab., N.Y.

B-Chain Insulin Gene

The chemical synthesis of a gene coding for the B-chain of human insulin is outlined in formula 6, the roman numerals indicating the portions as synthesized by the phosphotriester method (H. M. Hsiung, S. A. Narang et al., Nucleic Acids Res. 6, 1371, 1979) and their sequence of joining by DNA ligase. The portions can be joined by DNA ligase, and the DNA partial duplex completed by repair synthesis to form the full duplex, in a manner similar to the assembly of the insulin A-chain fragments. Both a start signal and a stop signal adaptor can be added to the two ends of the synthetic gene as in the construction of the insulin A-chain gene. The synthesized B-chain gene, with protruding cohesive ends as in formula 6, can be ligated to the same 4000-nucleotide-long duplex plasmid DNA as for the A-chain and the hybrid used to transform $E.$ $coli$ strain 5346 cells as before.

An adapted B-chain gene based on the structure as in formula 6, was constructed by preparing segments and joining in sequence as shown by roman numerals, ligated to the plasmid, and transferred into host cells as described above. Transformed cells and the presence of the B-chain gene therein, were identified and confirmed as before.

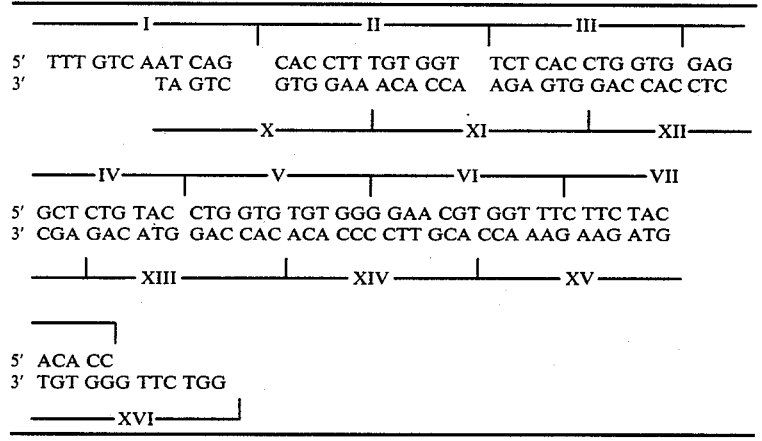

Formula 6
Sequence of fragments I to VII and X to XVI which were completed to constitute human-like insulin B-chain DNA coding sequence.

Purified insulin A-chain protein, isolated from $E.$ $coli$ carrying the A-chain gene, can be converted to the S-sulfonate form and combined in vitro with the SH-form of similarly-isolated B-chain protein, or conversely, the B-chain in the S-sulfonate form can be combined in vitro with the SH-form of similarly isolated A-chain protein, according to the method of Katsoyannis et al., in J. Am. Chem. Soc. 95, 6427, 1973, to form human-type insulin.

The host cells (any cell that allows the DNA to enter, to replicate and to produce gene-directed product) into which the adapted gene-cloning vehicle hybrid is transferred can be chosen from among various other bacteria, such as $Bacillus$ $subtilis;$ various fungi, e.g. yeasts, particularly baker's or brewer's yeasts; or plant or animal cells.

The transformed $E.$ $coli$ cells carrying the insulin A-chain and B-chain gene are maintained at the Biochemistry Department, Cornell University, Ithaca, N.Y., and are available upon request subject only to present or future Federal Government regulations on the handling of such materials.

We claim:

1. Synthetic adaptor oligodeoxynucleotide molecules, for facilitating insertion of DNA information sequences into a cloning vehicle, and transcription and translation of said sequences in a host cell; each adaptor consisting of from about 8 to 20 nucleotide base pairs or incomplete pairs in their structure and consisting essentially of:
   (a) a recognition site for a restriction endonuclease, and
   (b) a signal for protein synthesis, selected from a start signal and a stop signal, said start signal being downstream of said recognition site and said stop signal being upstream of said recognition site; said signal being at an end of the adaptor molecule.

2. The start signal adaptor molecules of claim 1 including at least one additional base between each start signal and the recognition site to correct the frame shift of a DNA information sequence with inappropriate reading frame.

3. Adaptor oligodeoxynucleotide molecules useful for attaching DNA information sequences to a cloning vehicle which are synthetic symmetrical DNA duplexes containing a recognition site for a restriction endonuclease and having duplicated signals for protein synthesis, selected from a start signal and stop signal, at each end, each complementary nucleotide strand consisting of from about 8 to 20 nucleotides and having complete palindromic symmetry to its opposite strand, with both halves of the duplex being identical on 180° rotation of one half.

4. Start signal adaptor molecules of claim 3 including additional nucleotide bases between each start signal and the central recognition site, to correct the frame shift of a DNA information sequence with inappropriate reading frame.

5. The start signal adaptor molecule of claim 1 wherein said start signal comprises the ATG codon or the GTG codon.

6. The stop signal adaptor molecules of claim 1 wherein said stop signal comprises at least one codon selected from the group TGA, TAA, and TAG.

7. The adaptor molecule of claim 3 comprising one of the duplex structures:

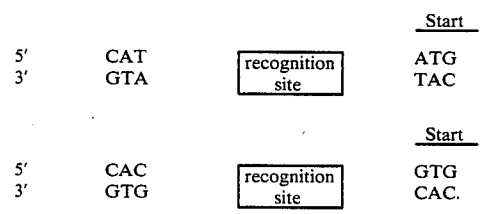

8. The start signal adaptor of claim 7 comprising the structure:

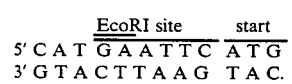

9. The start signal adaptor of claim 4 comprising the structure:

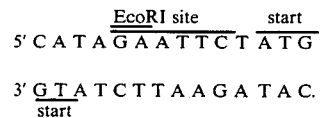

10. The start signal adaptor of claim 4 comprising the structure:

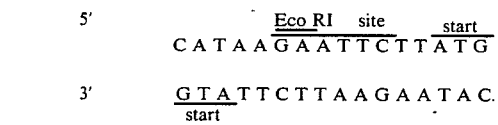

11. The start signal adaptor of claim 5 including a strong promoter sequence for mRNA transcription located upstream from the start signal and the recognition site.

12. The stop signal adaptor of claim 6 comprising one of the duplex structures:

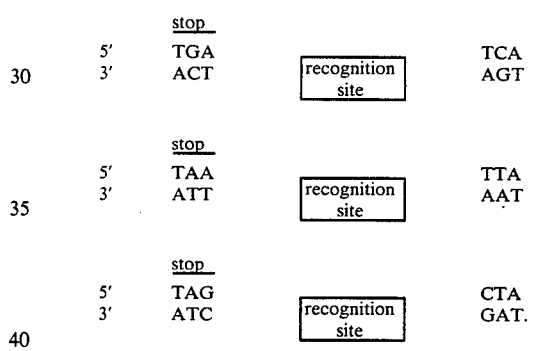

13. The stop signal adaptor of claim 12 wherein the recognition site has the following structure:

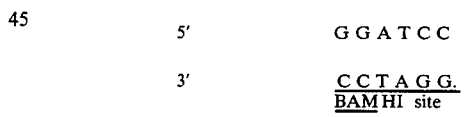

14. The stop signal adaptor molecule of claim 6 having the structure:

15. The stop signal adaptor molecule of claim 6 having the structure:

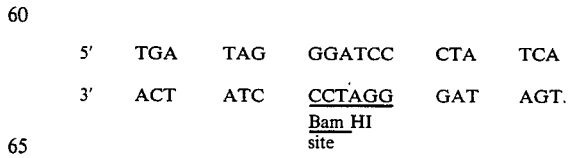

16. The partial duplex DNA molecule, adapted for forming insulin A-chain gene, having the structure:

```
     1                                                              43
5'  GGC.ATT.GTG.GAG.CAG.TGC.TGC.ACC.AGC.ATC.TGC.TCC.CTC.TAC.C
                                    36                    21
3'                                  TAG.ACG.AGG.GAG.ATG.G
          20                        1
          TT.GAC.CTC.TTG.ATG.ACG.TTG.
```

* * * * *

UNITED STATES PATENT AND TRADEMARK OFFICE
CERTIFICATE OF CORRECTION

PATENT NO. : 4,617,384

DATED : October 14, 1986

INVENTOR(S) : Saran A. Narang et al.

It is certified that error appears in the above-identified patent and that said Letters Patent is hereby corrected as shown below:

Col. 1, line 7, after "abandoned." insert --This invention was made with Government support under Grant No. NIH-AM 21801 awarded by the Department of Health and Human Services. The Government has certain rights in the invention.--.

Claim 14, line 4, change "CAT" to --GAT--.

Claim 16, line 5, at the beginning of the line insert --3' (cont'd.)--.

Signed and Sealed this

Third Day of March, 1987

Attest:

DONALD J. QUIGG

Attesting Officer

Commissioner of Patents and Trademarks